US005830847A

United States Patent [19]
Letarte et al.

[11] Patent Number: 5,830,847
[45] Date of Patent: Nov. 3, 1998

[54] SOLUBLE TGF-β-BINDING ENDOGLIN POLYPEPTIDES AND HOMODIMERS

[75] Inventors: Michelle Letarte, Toronto, Canada; Joan Massague, New York, N.Y.; Carmelo Bernabeu, Madrid, Spain; Sela Cheifetz, Concord, Canada

[73] Assignee: HSC Research & Development Limited Partnership, Canada

[21] Appl. No.: 968,953

[22] Filed: Oct. 30, 1992

[51] Int. Cl.[6] .................. C07K 14/715; A61K 38/17; C12N 15/12

[52] U.S. Cl. ................... 514/2; 514/8; 530/350; 530/395

[58] Field of Search .................. 530/395, 350; 514/2, 8; 435/69.2, 69.1

[56] References Cited

U.S. PATENT DOCUMENTS 5,284,931  2/1994  Springer et al. ............ 424/139.1

FOREIGN PATENT DOCUMENTS

WO 90/00194  6/1989  WIPO .
9110727  7/1991  WIPO .

OTHER PUBLICATIONS

Bodmer et al., "Transforming Growth Factor–Beta Bound to Soluble Derivatives of the Beta Amylois Precursor Protein of Alzheimer's Disease" *Biochem. Biophys. Res. Commun.* 171(2):890–897 (1990).

Buhring et al., "Endoglin is Expressed on a Subpopulation of Immature Erythroid Cells of Normal Human Bone Marrow" *Leukemia* 5:841–847 (1991).

Cheifetz et al., "The Transforming Growth Factor–β Receptor Type III Is a Membrane Proteoglycan" *J. Biol. Chem.* 263(32):16984–16991 (1988).

Cheifetz et al., "A Surface Component on $GH_3$ Pituitary Cells That Recognizes Transforming Growth Factor–β, Activin, and Inhibin" *J. Biol. Chem.* 263(33):17225–17228 (1988).

Cheifetz et al., "Transforming Growth Factor–β (TGF–β) Receptor Proteoglycan" *J. Biol. Chem.* 264(20):12025–12028 (1989).

Cheifetz et al., "Isoform–specific Transforming Growth Factor–βBinding Proteins with Membrane Attachments Sensitive to Phosphatidylinositol–specific Phospholipase C" *J. Biol. Chem.* 266(31):20767–20772 (1991).

Danielpour et al., "Differential Inhibition of Transforming Growth Factor β1 and β2 Activity by $\oplus_1$–Macroglobulin" *J. Biol. Chem.* 265(12):6973–6977 (1990).

Fava et al., "Fibronectin–Associated Transforming Growth Factor" *J. Cellular Physiology* 131:184–189 (1987).

Gougos et al., "Identification of distinct epitopes of engoglin, an RGD–containing glycoprotein of endothelial cells, leukemic cells, and syncytiotrophoblasts" *International Imunology* 4(1):83–92 (1992).

(List continued on next page.)

*Primary Examiner*—David L. Fitzgerald
*Attorney, Agent, or Firm*—Campbell & Flores LLP

[57] ABSTRACT

This invention provides a novel purified TGF-β-binding glycoprotein, endoglin, an isolated nucleic acid molecule that encodes an amino acid sequence corresponding to the TGF-β-binding glycoprotein, soluble endoglin-derived polypeptide, and fragments thereof. A pharmaceutical composition which comprises the endoglin-derived polypeptide purified by applicants or produced by applicants' recombinant methods and a pharmaceutically acceptable carrier is further provided as well as methods of treating patients which comprise administering to the patient the pharmaceutical composition of this invention.

14 Claims, 3 Drawing Sheets

OTHER PUBLICATIONS

Gougos et al., "Identification of a Human Endothelial Cell Antigen With Monoclonal Antibody 44G4 Produced Against a Pre–B Leukemic Cell Line" *J. of Immunology* 141:1925–1933 (1988).

Gougos et al., "Biochemical Characterization of the 44G4 Antigen from the Hoon Pre–B Leukemic Cell Line" *J. of Immunology* 141:1934–1940 (1988).

Keski–Oja et al., "Transforming Growth Factors and Control of Neoplastic Cell Growth" *J. Cellular Biochemistry* 33:95–107 (1987).

LaMarre et al., "$\alpha_2$–Macroglobulin and Serum Preferentially Counteract the Mitoinhibitory Effect of Transforming Growth Factor–$\beta2$ in Rat Hepatocytes" *Laboratory Investigation* 62(5):545–551 (1990).

Lastres et al., "Regulated expression on human macrophages of endoglin, an Arg–Gly–Asp–containing surface antigen" *Eur. J. Immunol.* 22:393–397.

Lin et al., "Expression Cloning of the TGF–$\beta$ Type II Receptor, a Functional Transmembrane Serine/Threonine Kinase" *Cell* 68:775–785 (1992).

Lopez–Casillas et al., "Structure and Expression of the Membrane Proteoglycan Betaglycan, a Component of The TGF–$\beta$ Receptor System" *Cell* 67:785–795 (1991).

MacKay et al., "Identification of Disulfide–linked Transforming Growth Factor–$\beta1$–specific Binding Proteins in Rat Glomeruli" *J. Biol. Chem.* 265(16):9351–9356 (1990).

MacKay et al., "Novel 150– and 180–kDa Glycoproteins That Bind Transforming Growth Factor (TGF)–$\beta1$ but Not TGF–$\beta2$ Are Present in Several Cell Lines" *J. Biol. Chem.* 266(15):9907–9911 (1991).

Massaqué, Joan, "The TGF–$\beta$ Family of Growth and Differentiation Factors" *Cell* 49:437–438 (1987).

Massagué, Joan, "The Transforming Growth Factor–$\beta$ Family" *Annu. Rev. Cell Biol.* 6:597–641 (1990).

Murphy–Ullrich et al., *J. Cell. Biol.* 111:148a (1990).

O'Connell et al., "Endoglin: a 180–kD endothelial cell and macrophage restricted differentiation molecule" *Clin. Exp. Immunol.* 90:154–159 (1992).

O'Connor–McCourt et al., "Latent Transforming Growth Factor–$\beta$ in Serum" *J. Biol. Chem.* 262(29) 14090–14099 (1987).

O'Grady et al., "Purification of a New Type High Molecular Weight Receptor (Type V Receptor) of Transforming Growth Factor $\beta$ (TGF–$\beta$) from Bovine Liver" *J. Biol. Chem.* 266(13):8583–8589 (1991).

Paralkar et al., *Dev. Biol.* 143:303–308 (1991).

Quackenbush et al., "Differential Localization Within Human Kidney of Five Membrane Proteins Expressed on Acute Lymphoblastic Leukemia Cells" *J. of Immunology* 136(1):118–124 (1988).

Quackenbush et al,. "Identification of Several Cell Surface Proteins of Non–T, Non–B Acute Lymphoblastic Leukemia By Using Monoclonal Antibodies" *J. of Immunology* 134(2):1276–1285 (1985).

Segarini et al., "The High Molecular Weight Receptor to Transforming Growth Factor–$\beta$ Contains Glycosaminoglycan Chains" *J. Biol. Chem.* 263(17):8366–8370 (1988).

Sporn et al., "Some Recent Advances in the Chemistry and Biology of Transforming Growth Factor–Beta" *J. Cell Biology* 105:1039–1045 (1987).

Wang et al., "Expression Cloning and Characterization of the TGF–$\beta$ Type III Receptor" *Cell* 67:797–805 (1991).

Yamaguchi et al., "Negative regulation of transforming growth factor–$\beta$ by the proteoglycan decorin" *Nature* 346:281–284 (1990).

Andres et al., *J. Cell Biol.* 109:31317–31345 (1989).

Gougos, A, et al (1990) J. Biol. Chem. 265: 8361–64.

Sutcliffe, J.G., et al (1983) Science 219: 660–66.

Letarte, M., et al. (1992) J. Cell Biochem. Suppl. O (16, pt. F): 158, abst. No. 214.

Cheifetz, S., et al. (1992) J. Biol. Chem. 267: 19027–30.

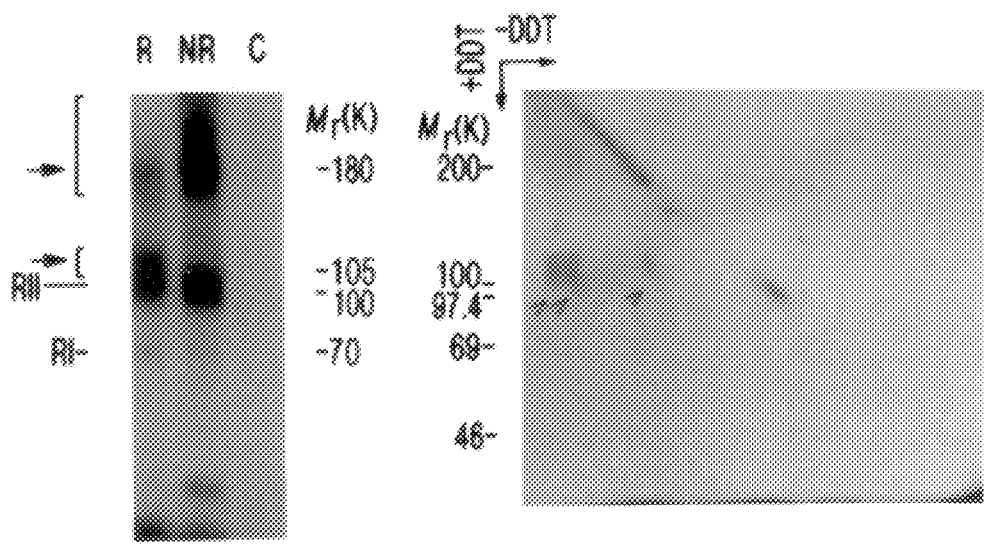
FIG. 2A
FIG. 2B
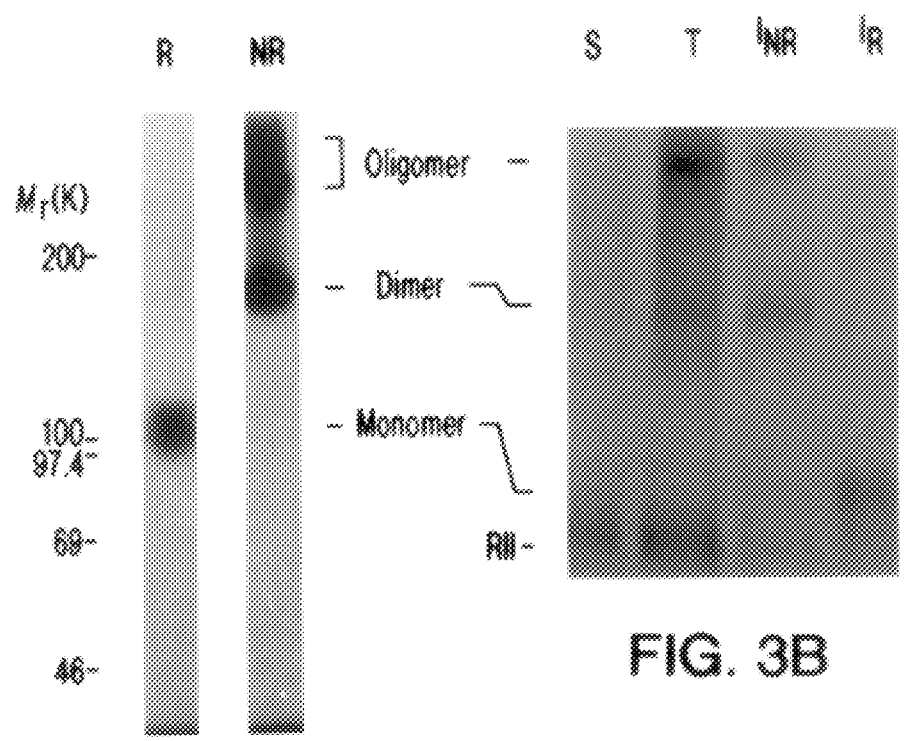
FIG. 3A
FIG. 3B

SOLUBLE TGF-β-BINDING ENDOGLIN POLYPEPTIDES AND HOMODIMERS

This invention was made in part with Government support under Grant No. CA 34610, from the National Institutes of Health. The Government may have certain rights in this invention.

FIELD OF THE INVENTION

The present invention relates to cell biology and to methods of modifying the biological activity of cell regulatory factors. More specifically, the present invention relates to a novel TGF-β-binding glycoprotein.

Throughout this application various publications are referenced within parentheses. The disclosures of these publications in their entireties are hereby incorporated by reference in this application in order to more fully describe the state of the art to which this invention pertains.

BACKGROUND OF THE INVENTION

Glycoproteins, in which one or more carbohydrate units have been attached covalently to the protein by posttranslational processing are widely distributed. Several secretory proteins, including the immunoglobulins, are glycoproteins, as are most components of plasma membranes such as cell membrane receptors, where the carbohydrates can be involved in cell-to-cell adhesion.

Transforming growth factor β (TGF-β) refers to a family of multi-functional cell regulatory factors produced in various forms by many cell types (for review see Sporn et al,. J. Cell Biol., 105:1039 (1987)). Five distinct isoforms of TGF-β have been identified. TGF-β1 and TGF-β2 have been characterized in detail. TGF-β is the subject of U.S. Pat. Nos. 4,863,899; 4,816,561 and 4,742,003 which are incorporated herein by reference. TGF-β binds to cell surface receptors present on various types of cells. TGF-β potentiates or inhibits the response of most cells to other growth factors, depending on the cell type. TGF-β also regulates differentiation of some cell types, either promoting or inhibiting proliferation of the cell. A marked effect of TGF-β is the promotion of cellular production of extracellular matrix proteins and their receptors (for a review see Keski-Oja et al., J. Cell Biochem., 33:95 (1987); Massague, Cell 49:437 (1987); Roberts and Sporn, "Peptides Growth Factors and Their Receptors", Springer-Verlag (1989)).

Notwithstanding the beneficial and essential cell regulatory functions served, TGF-β regulatory activity can prove detrimental to its host organism. For example, whereas growth and proliferation of mesenchymal cells is stimulated by TGF-β, some tumor cells may also be stimulated, using TGF-β as an autocrine growth factor. In other cases the inhibition of cell proliferation by TGF-β similarly proves detrimental to its host organism. An example would be the prevention of new cell growth to assist in repair of tissue damage. The stimulation of extracellular matrix production by TGF-β is essential for wound healing. However, in some cases, the TGF-β response is uncontrolled and an excessive accumulation of extracellular matrix results. An example of excessive accumulation of extracellular matrix is glomerulonephritis and scar tissue formation.

The transforming growth factor-β receptor system in most mesenchymal and epithelial cells consists of several components (Massague, J. Ann. Rev. Cell Biol., 6:597 (1990); Lin, H. Y. et al., Cell, 68:775 (1992); Georgi, L. L. et al., Cell, 61:635 (1990); Mathews, L. S. et al., Cell, 65:973 (1991); Attisano, L. et al., Cell. 68::97 (1992); Lopez-Casillas et al., Cell, 67:785 (1991) and Wang et al., Cell, 67:796 (1991) all of which are incorporated herein by reference), one of which is betaglycan, a membrane-anchored proteoglycan. In addition to betaglycan, the TGF-β receptor system in most mesenchymal and epithelial cells consists of the type I receptor, a 53-kDa glycoprotein whose structure has not been determined yet, and the type II receptor, which belongs to the protein serine/threonine kinase receptor family. Additional cell surface TGF-β-binding proteins, some of which have a more restricted distribution, have also been described.

Thus, a need exists to develop compounds that can modify the effects of cell regulatory factors such as TGF-β. The present invention satisfies this need and provides related advantages as well.

SUMMARY OF THE INVENTION

The present invention provides a novel purified TGF-β-binding glycoprotein. This novel human protein, endoglin, is expressed at high levels on human vascular endothelial cells.

Further provided by the present invention are methods of treating pathologic conditions mediated by TGF-β regulatory activity by contacting the TGF-β with an effective amount of purified endoglin-derived polypeptide or any fragment thereof having the ability to bind TGF-β. Thus, intact, native endoglin and soluble fragments thereof are useful in these methods. This invention provides a method of preparing and purifying soluble endoglin-derived polypeptide. Isolated nucleic acids encoding the novel TGF-β-binding glycoprotein and soluble endoglin-derived polypeptides are also provided, as well as vectors containing the nucleic acids and recombinant host cells transformed with such vectors.

BRIEF DESCRIPTION OF THE FIGURES

FIGS. 2A and 2B show cell surface TGF-β1-binding proteins expressed by HUVEC. Near confluent cultures of HUVECs were affinity-labeled by incubation with 100 pM $^{125}$I-TGF-β1 followed by chemical cross-linking with 0.16 mM disuccinimidyl suberate. FIG. 2A shows Triton X-100 extracts of affinity-labeled HUVEC were resolved on SDS-PAGE gels under reducing (R) or nonreducing (NR) conditions. Lane C contains extract from cells affinity-labeled in the presence of excess unlabeled TGF-β1. The migration position of TGF-β receptors I (RI) and II (RII) are indicated. Arrow, the major affinity-labeled proteins of 180 kDa and higher molecular mass apparent on nonreducing gels. Arrowhead, the affinity-labeled proteins of 110–120 kDa seen on reducing gels. FIG. 2B shows detergent extracts of affinity-labeled HUVEC were resolved under nonreducing conditions on a first gel that was then resolved under reducing conditions in the second dimension as previously described. The 110–120-kDa labeled species migrating off-the-diagonal are indicated (arrowheads).

FIGS. 3A and 3B show specific immunoprecipitation of TGF-β1-endoglin complexes. HUVECs were affinity-labeled with 100 pM $^{125}$I-TGF-β1 as described in FIG. 1. FIG. 3A shows detergent extracts of affinity-labeled cells were incubated with mAb 44G4 and immune complexes were collected on protein G-Sepharose. After washes, equal aliquots of the samples were analyzed under reducing (R) or non-reducing (NR) conditions by SDS-PAGE (5–8% polyacrylamide gradient gels). FIG. 3B shows affinity-labeled HUVEC lysates were maximally depleted of endoglin by two successive 45 min incubations at 4° C. with 100 μl of 44G4-IgG-Sepharose. S) supernatant after second immunoprecipitation. I) the first 44G4 immunoprecipitation which contained 83% of the endoglin. T) corresponding amount of total extract used for the depletion experiment. All samples were analyzed under nonreducing conditions on SDS-PAGE with the exception of $I_R$, which was run under reducing conditions. The migration positions of TGF-β receptor II (RII), and endoglin monomer, dimer, and oligomer are indicated.

FIG. 5A shows COS-M6 cells transfected with endoglin vector were affinity-labeled with 150 pM $^{125}$I-TGF-β1 alone or in the presence of 1 or 10 nM unlabeled TGF-β1, -β2 or -β3. FIG. 5B shows HUVEC were affinity-labeled with 100 pM $^{125}$1I-TGF-β1 alone or in the presence of 5 nM unlabeled TGF-β1 or TGF-β2. Lysates from these cells were immunoprecipitated with MAb 44G4. Immunoprecipitates were fractionated under reducing conditions on SDS-PAGE gels. The region of the gels containing monomeric endoglin is shown along with the migration position of 100-kDa marker.

DETAILED DESCRIPTION OF THE INVENTION

Figure 1:
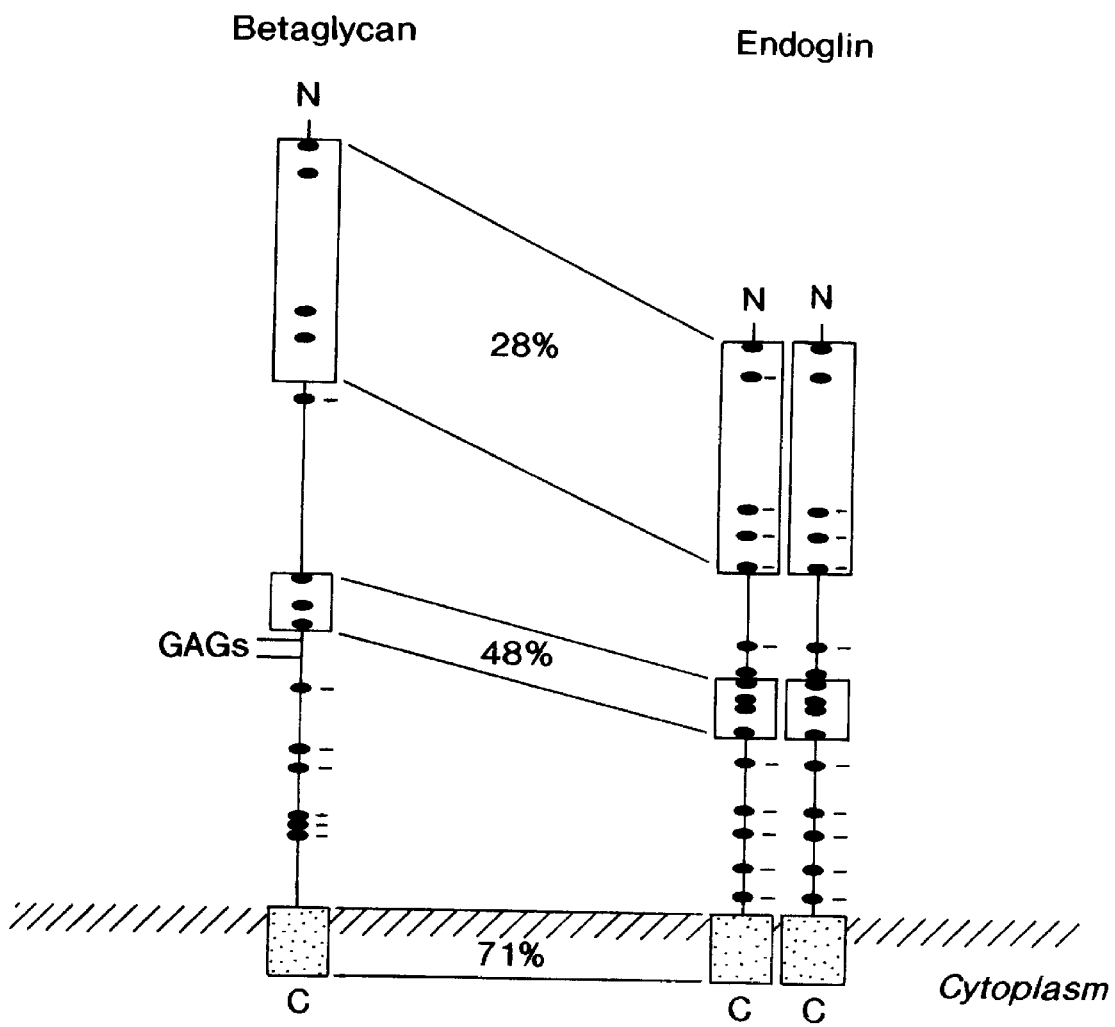
FIG. 1 shows the domain structures of betaglycan and endoglin. Shown is a schematic representation highlighting regions of similarity between the linear sequences of betaglycan, an 853-amino acid transmembrane proteoglycan, and endoglin, a disulfide-linked transmembrane protein composed of two identical subunits of 633 amino acids each. The transmembrane and short cytoplasmic regions (dark shaded box) of endoglin have a high level of sequence similarity to the corresponding regions of betaglycan. Two regions of weaker similarity are detected in the ectodomains of these proteins (light shaded boxes). Numbers represent the percent amino acid sequence similarity between the indicated domains of betaglycan and endoglin. Closed ovals represent positions of cysteine residues. Two putative sites for glycosaminoglycan chain attachment in betaglycan are indicated.

Endoglin is a homodimeric membrane glycoprotein composed of disulfide-linked subunits of 95 kDa. It is expressed in human pre-erythroblasts, macrophages, leukemic cells of the lymphoid and myeloid lineages, and at higher levels in syncytiotrophoblast of term placenta and vascular endothelial cells. A relationship between human endoglin and the TGF-β receptor system was discovered with the molecular cloning of the rat TGF-β-binding proteoglycan, betaglycan (also known as the type III TGF-β receptor), which revealed that the transmembrane domain and the relatively short (43 amino acid) cytoplasmic tail of this protein were remarkably similar (71% amino acid sequence similarity and 63% amino acid identity) to the corresponding regions in endoglin (see FIG. 1). The extracellular domains of these two proteins show limited homology in primary structure, and while endoglin is not a proteoglycan, it does contain N- and 0-linked oligosaccharides.

The sequence of endoglin revealed a Type I integral membrane protein of 68,051 Daltons. The extracellular region of 561 amino acids contains 4 potential N-linked glycosylation sites and an 0-glycan domain rich in serine and threonine residues proximal to the plasma membrane: a single hydrophobic transmembrane region is followed by a 47-amino acid cytoplasmic tail. The presence of an Arg-Gly-Asp (RGD) motif in an accessible region of the polypeptide led to the suggestion that this integral membrane protein may play a role in RGD-mediated cellular adhesion events. Endoglin contains an RGD sequence and so is potentially involved in RGD-mediated cellular adhesion, whereas betaglycan does not contain this sequence.

Accordingly, the present invention provides a soluble endoglin-derived polypeptide that binds TGF-β. The full-length soluble endoglin-derived polypeptide comprises the 561 amino acids of the extracellular domain of the mature endoglin polypeptide, an integral membrane protein, which consists of 633 amino acids in total. The nucleic acid sequence encoding the 633 amino acid mature endoglin a polypeptide is identified as SEQ ID NO. 1 (SEQ ID NOS:1–2). The nucleic acid sequence encoding the soluble endoglin-derived polypeptide is included within the sequence set forth as SEQ ID NO:1 (from about amino acid number 1 to about amino acid number 561).

As used herein, the term "purified" means that the molecule or compound is substantially free of contaminants normally associated with a native or natural environment. For example, the mature 633 amino acid protein can be obtained from a number of methods. The methods available for the purification of membrane proteins include precipitation, gel filtration, ion-exchange, reversed-phase, and affinity chromatography. Other well-known methods are described in Deutscher et al., *Guide to Protein Purification: Methods in Enzymology* Vol. 182, (Academic Press 1990), which is incorporated herein by reference. Alternatively, a purified polypeptide of the present invention can also be obtained by well-known recombinant methods as described, for example, in Maniatis et al., *Molecular Cloning: A Laboratory Manual* 2d ed. (Cold Spring Harbor Laboratory 1989), also incorporated herein by reference. An example of this means for preparing soluble endoglin-derived polypeptide is to express nucleic acid encoding the soluble endoglin in a suitable host cell, such as a bacterial, yeast or mammalian cell, using methods well known in the art, and recovering the expressed soluble protein, again using methods well known in the art. The soluble polypeptide and biologically active fragments thereof can also be produced by chemical synthesis. Synthetic polypeptides can be produced using Applied Biosystems, Inc. Model 430A or 431A automatic polypeptide synthesizer and chemistry provided by the manufacturer. The soluble polypeptide can also be isolated directly from cells which have been transformed with the expression vectors described below in more detail.

As used herein, endoglin-derived polypeptide means a polypeptide having the amino acid sequence substantially the same as the 633 amino acid sequence shown as SEQ ID NO:2, or an active fragment thereof. As used herein the term "soluble endoglin-derived polypeptide" refers to a soluble, biologically active fragment of the human endoglin polypeptide expressed by the extracellular domain of the nucleic acid. As used herein, an "active fragment" or "biologically-active fragment" refers to any portion of the endoglin polypeptide shown in as SEQ ID NO:1 that bind to TGF-β. Methods of determining whether a polypeptide can bind TGF-β are well known to those of skill in the art, for example, as set forth herein.

The invention also encompasses nucleic acid molecules which differ from that of the nucleic acid molecule shown as SEQ ID NO:1 but which produce the same phenotypic effect. These altered, but phenotypically equivalent nucleic acid molecules are referred to as "equivalent nucleic acids". This invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention. As used herein, the term "nucleic acid" encompasses RNA as well as single and double-stranded DNA and cDNA. In addition, as used herein, the term "polypeptide" encompasses any naturally occurring allelic variant thereof as well as man-made recombinant forms.

This invention provides an isolated nucleic acid molecule encoding a human soluble endoglin-derived polypeptide. As used herein, the term "isolated nucleic acid molecule" means a nucleic acid molecule that is in a form that does not occur in nature. One means of isolating a human endoglin nucleic acid is to probe a human cDNA expression library with a natural or artificially designed antibody to endoglin, using methods well known in the art (see Gougos, A. et al., J. Biol Chem., 265:8361 (1990) which is incorporated herein by reference). DNA and cDNA molecules which encode human endoglin polypeptides can be used to obtain complementary genomic DNA, cDNA or RNA from human, mammalian or other animal sources.

The invention further provides the isolated nucleic acid molecule operatively linked to a promoter of RNA transcription, as well as other regulatory sequences. As used herein, the term "operatively linked" means positioned in such a manner that the promoter will direct the transcription of RNA off of the nucleic acid molecule. Examples of such promoters are SP6, T4 and T7. Vectors which contain both a promoter and a cloning site into which an inserted piece of DNA is operatively linked to that promoter are well known in the art. Preferable, these vectors are capable of transcribing RNA in vitro or in vivo. Examples of such vectors are the pGEM series (Promega Biotec, Madison, Wis.).

This invention provides a vector comprising this isolated nucleic acid molecule such as DNA, cDNA or RNA encoding a soluble endoglin-derived polypeptide. Examples of vectors are viruses, such as bacteriophages, baculoviruses and retroviruses, cosmids, plasmids (such as pcEXV-2) and other recombination vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColEl for proper episomal replication; versatile multiple cloning sites; and T7 and SP6 RNA promoters for in vitro transcription of sense and antisense RNA. Other means are available.

Also provided are vectors comprising a DNA molecule encoding a human soluble endoglin-derived polypeptide, adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding soluble endoglin polypeptide as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis et al. supra. 1989). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example the methods described above for constructing vectors in general. Expression vectors are useful to produce cells that express the polypeptide.

This invention provides a mammalian cell containing a cDNA molecule encoding a human soluble endoglin-derived polypeptide. An example is a mammalian cell comprising a plasmid adapted for expression in a mammalian cell. The plasmid has a cDNA molecule encoding a soluble endoglin-derived polypeptide and the regulatory elements necessary for expression of the polypeptide. Various mammalian cells may be utilized as hosts, including, for example, mouse fibroblast cell NIH3T3, CHO cells, HeLa cells, Ltk- cells, etc. Expression plasmids such as those described supra can be used to transfect mammalian cells by methods well known in the art such as calcium phosphate precipitation, DEAE-dextran, electroporation or microinjection.

This invention provides a pharmaceutical composition containing a pharmaceutical carrier and any of a purified, soluble polypeptide, an active fragment thereof, or a purified, mature protein and active fragments thereof, alone or in combination with each other. These polypeptides or proteins can be recombinantly derived, chemically synthesized or purified from native sources. As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

Also provided are antibodies having specific reactivity with the endoglin-derived TGF-β-binding polypeptides of the subject invention, such as anti-endoglin antibody 44G4, or any antibody having specific reactivity to a TGF-β-binding endoglin polypeptide. Active fragments of antibodies are encompassed within the definition of "antibody." The antibodies of the invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The polypeptide, particularly soluble endoglin-derived polypeptide of the present invention, can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical synthesis or recombinant methods described, for example, in Maniatis et al., supra, incorporated herein by reference. The antibodies can be used for determining the presence or purification of the soluble endoglin-derived polypeptide of the present invention. With respect to the detecting of such polypeptides, the antibodies can be used for in vitro diagnostic or in vivo imaging methods.

Immunological procedures useful for in vitro detection of the target soluble endoglin-derived polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

This invention provides a method of modifying a biological function mediated by the regulatory activity of TGF-β which comprises contacting a suitable sample containing TGF-β with an effective amount of a biologically active endoglin-derived polypeptide or a pharmaceutical composition described above. As used herein, "an effective amount" refers to an amount of the polypeptide sufficient to bind to TGF-β and thereby prevent or inhibit its regulatory activity. This method is especially useful for modifying the regulatory activity of TGF-β1 or TGF-β3. Examples of regulatory activities include, but are not limited to stimulation of cell proliferation, cell growth inhibition, or promotion of extracellular matrix proteins.

An effective amount is any amount that is effective to modify the biological function mediated by the regulatory activity of TGF-β. The method can be practiced in vitro or in vivo. If the method is practiced in vitro, contacting is effected by incubating the sample with a polypeptide, a protein or a pharmaceutical composition as described above.

However, in a preferred embodiment the contacting is effected in vivo by administering a polypeptide, a protein or a pharmaceutical composition, as described above, to a subject, e.g., a human patient.

Methods of administration are well known to those of skill in the art and include, but are not limited to administration orally, intravenously or parenterally.

Administration will be in such a dosage such that the regulatory activity is effectively modified. Administration can be effected continuously or intermittently such that this amount is effective for its intended purpose.

This invention also provides a method of treating a pathologic condition caused by a TGF-β-regulated activity comprising contacting the TGF-β with any of a purified soluble endoglin-derived polypeptide, an active fragment thereof, an endoglin-derived polypeptide or an active fragment thereof. The TGF-β is bound with said polypeptide to thereby treat the pathologic condition mediated by TGF-β regulatory activity. As used herein, "pathologic conditions" refers to any pathology arising from TGF-β-induced regulatory activity. For example, growth and proliferation of mesenchymal cells is stimulated by TGF-β, however some tumor cells may also be stimulated thus using TGF-β as an autocrine growth factor. An example of inhibitory conditions are the prevention of new cell growth to assist in repair of tissue damage. The stimulation of extracellular matrix production by TGF-β is essential for wound healing. However, in some cases, the TGF-β response is uncontrolled and an excessive accumulation of extracellular matrix results. An example of excessive accumulation of extracellular matrix is glomerulonephritis. Additional examples of pathologies include cancer, rheumatoid arthritis and atherosclerosis.

In a preferred embodiment, the method is practiced by administering to a subject, e.g., a human patient, an effective amount of a purified endoglin protein or an endoglin-derived soluble polypeptide or a biologically active fragment thereof, or the pharmaceutical composition described above. Methods of administration are outlined supra.

It is understood that modifications which do not substantially affect the activity of the various molecules of this invention are also included within the definition of said molecules.

The following examples are intended to illustrate but not limit the present invention.

EXAMPLE I

Cell Culture and Transfections

Human umbilical vein endothelial cells (HUVEC, CRL 1730, ATCC) were maintained in α-minimal essential media supplemented according to supplier's instructions or prepared from umbilical veins as previously described (Gougos, A. et al., J.Immunol., 141:1925 (1988)). Similar results were obtained using cells from either source. COS-M6 cells, maintained in Dulbecco's modified Eagle's medium supplemented with 10% bovine serum, were transfected with a cDNA encoding full-length endoglin ligated into the EcoRI site of the mammalian expression vector pcEXV (Miller, J. et al., J.Exp.Med., 164:1478 (1986)) or with a control vector without cDNA insert (pcMV5; Lopez-Casillas, F. et al., Cell, 67:785 (1991)) by the DEAE-dextran-chloroquine procedure (Seed, B., et al., Proc.Natl.Acad.Sci. USA, 84:3365 (1987)). 24 hours post-transfection, cells were trypsinized and reseeded into multicluster dishes and allowed to grow an additional 48 hours before being affinity-labeled with $^{125}$I-TGF-β1 as described below.

EXAMPLE II

Receptor Affinity Labeling and Immunoprecipitation

TGF-β1 and TGF-β2 were purchased from R & D Systems (Minneapolis, Minn.) and TGF-p3 was obtained from Oncogene Science (Manhassett, N.Y.). $^{125}$I-TGF-β1 used in these studies was prepared by the chloramine-T method as previously described (Cheifetz, S. et al., J.Biol.Chem., 265:20533 (1990)) or purchased from Amersham Corp.; both preparations gave identical results. The conditions for affinity labeling cell monolayers with $^{125}$I-TGF-β1 and disuccinimidyl suberate (Pierce Chemical Co.) have been described previously (Massague, J., Methods Enzymol., 146:174 (1987)). The concentrations of $^{125}$I-TGF-β1 and competing unlabeled ligands used for each experiment are indicted in the figure legends. Triton X-100 extracts of the affinity-labeled cells were either analyzed directly on sodium dodecyl sulfate-polyacrylamide gels (SDS-PAGE) or first incubated with monoclonal antibody (mAb) 44G4 directed against human endoglin (Quackenbush, E. J. et al., J.Immunol., 134:1276 (1985)) or with control antibody (see below). For immunoprecipitations, detergent extracts were diluted with an equal volume of phosphate-buffered saline containing 1% Triton X-100 and precleared by incubation for 20 min at 4° C. with protein G-Sepharose (Pharmacia LKB Biotechnology Inc.) prior to overnight incubation at 4° C. with mAb 44G4. Immune complexes were collected by incubation with protein G-Sepharose for 1 hour at 4° C. For some experiments, mAb 44G4 was used coupled to Sepharose. The immunoprecipitates were washed three times (saline with 1% Triton X-100) and then resolved by SDS-PAGE in the presence or absence of dithiothreitol (DTT) and visualized by autoradiography. Irrelevant mAb (44D7) used in control experiments to monitor specificity of the immunoprecipitations did not immunoprecipitate any affinity-labeled bands.

EXAMPLE III SDS-PAGE and 2D-Gel Analysis

Analysis of the affinity-labeled profile of HUVEC revealed that, like vascular endothelial cells from other sources, these cells have little or no betaglycan, which characteristically migrates as a diffuse band between 200 and 400 KDa on reducing SDS-PAGE (FIG. 2A). Instead, HUVEC expressed a disulfide-linked cell surface protein that, together with TGF-β receptors I and II, was affinity-labeled by crosslinking with $^{125}$I-TGF-β1. Receptors I and II were detected in HUVEC as labeled complexes of approximately 65 KDa and 100 KDa, which is similar to the size of these labeled receptors reported for other human cell lines. Comparison of the relative migration of the affinity-labeled proteins fractioned on SDS-PAGE revealed that the major affinity-labeled proteins of HUVEC migrated between 95–120 KDa on reducing gels whereas on non-reducing gels the major affinity-labeled proteins migrated between 100–110 KDa (presumed to be receptor II) and at 180 KDa and above (endoglin) (FIG. 2). This pattern indicated the presence of disulfide-linked TGF-β-binding proteins.

Resolution of these disulfide-linked TGF-β1 binding proteins on two-dimensional gels (FIG. 2B) confirmed that the disulfide-linked complexes (probably dimers and higher order oligomers) contained subunits of approximately 95 KDa (value estimated by subtracting the cross-linked TGF-β1 monomer mass 12.5 KDa from the reduced 110 KDa affinity-labeled complex). Together with the type II receptor, the disulfide-linked TGF-β1-binding proteins are the major affinity-labeled species expressed by HUVEC.

EXAMPLE IV

Immunoprecipitation with anti-endoglin mAb

To determine whether the disulfide-linked TGF-β-binding protein on endothelial cells was endoglin, affinity-labeled HUVEC extracts were immunoprecipitated with monoclonal antibody (mAb) 44G4 which is specific for human endoglin (Georgi, L. L. et al., Cell, 61:635 (1990); MacKay, K. et al., J.Biol.Chem., 266:9907 (1992); Merwin, J. R. et al., Am.J.Pathol., 138:37 (1991)). Electrophoretic analysis of these immunoprecipitates revealed a labeled protein complex whose subunit structure was similar to that of endoglin (FIG. 3A). Thus, under reducing conditions, a major affinity-labeled band of approximately 110 KDa was seen which migrated as complexes of 180 KDa and greater than 200 KDa when analyzed under non-reducing conditions. The higher order oligomers might contain multiple endoglin molecules crosslinked by TGF-β1, itself a disulfide-linked dimer. Repeated immunoprecipitation with 44G4-IgG-Sepharose completely depleted these labeled species from cell extracts (FIG. 3B). No affinity-labeled bands were immunoprecipitated from three other human cell lines (A549, Hep G2, MCF-7), which lack endoglin and were used as negative-controls for these experiments. Monoclonal antibodies specific to human endoglin and an endoglin expression vector thus demonstrate that endoglin is a major TGF-β-binding protein in human vascular endothelial cells.

EXAMPLE V

Ectopic Expression of Endoglin in Cells

Figure 4:
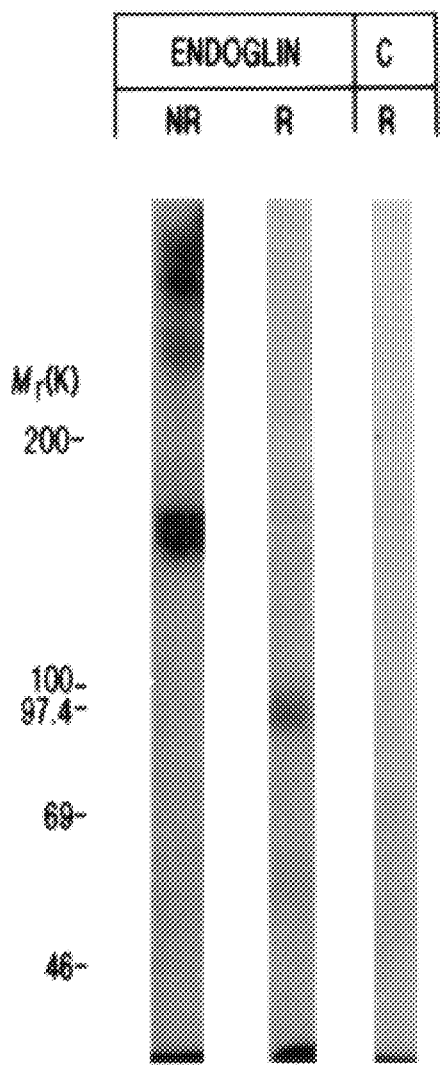
FIG. 4 shows that endoglin transiently expressed in COS-M6 cells binds TGF-β1. COS-M6 cells were transfected with a cDNA encoding full-length endoglin (Endoglin) or control vector (C). Cells were affinity-labeled with 150 pM $^{125}$I-TGF-β1 and the detergent extracts incubated with mAb 44G4 followed by protein G-Sepharose. Immunoprecipitated proteins were analyzed by SDS-PAGE under reducing (R) and nonreducing (NR) conditions and visualized by autoradiography.
Figures 5A, 5B:
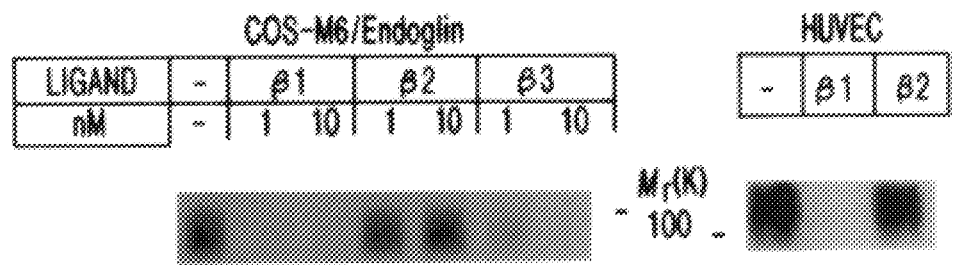
FIG. 5A and 5B show shows the specificity of endoglin for TGF-β isoforms assessed in COS cell transfectants and in HUVEC.

The identity of this dimeric TGF-β-binding protein of HUVEC with endoglin was confirmed by ectopically expressing the full-length endoglin cDNA in COS monkey kidney cells. After affinity-labeling with $^{125}$I-TGF-β1, a labeled species with the characteristics of endoglin could be specifically precipitated by mAb 44G4 only from the detergent extracts of endoglin transfectants (FIG. 4). Differences in glycosylation likely account for the smaller size of endoglin expressed in COS cells relative to endogenous endoglin of HUVEC.

Although the invention has been described with reference to the disclosed embodiments, it should be understood that various modifications can be made without departing from the spirit of the invention. Accordingly, the invention is limited only by the following claims.

We claim:

1. A purified, soluble polypeptide comprising the amino acid sequence of a polypeptide fragment of an endoglin protein, wherein said polypeptide fragment binds to TGF-β; provided that the soluble polypeptide does not comprise the complete amino acid sequence of an endoglin protein.

2. A soluble polypeptide according to claim 1, comprising the amino acid sequence of the extracellular domain of an endoglin protein.

3. A soluble polypeptide according to claim 1, comprising the amino acid sequence shown as residues 1 to 561 of SEQ ID NO: 2.

4. A soluble polypeptide according to claim 3, having the amino acid sequence shown as residues 1 to 561 of SEQ ID NO: 2.

5. A soluble polypeptide according to claim 1, in a form suitable for pharmaceutical use.

6. A pharmaceutical composition comprising a soluble polypeptide according to claim 5 and a pharmaceutically acceptable carrier.

7. A purified, soluble homodimer consisting of two polypeptides, each comprising the amino acid sequence of a polypeptide fragment of an endoglin protein, wherein said polypeptide fragment binds to TGF-β; provided that the homodimer does not consist of polypeptides comprising the complete amino acid sequence of an endoglin protein.

8. A homodimer according to claim 7, wherein each polypeptide comprises the amino acid sequence of the extracellular domain of an endoglin protein.

9. A homodimer according to claim 7, wherein each polypeptide comprises the amino acid sequence shown as residues 1 to 561 of SEQ ID NO: 2.

10. A homodimer according to claim 7, in a form suitable for pharmaceutical use.

11. A pharmaceutical composition comprising a homodimer according to claim 10 and a pharmaceutically acceptable carrier.

12. A purified, soluble endoglin-derived homodimer comprising two polypeptides, wherein each polypeptide consists of amino acids 1–561 set forth in SEQ ID NO:2.

13. A purified homodimer according to claim 12, in a form suitable for pharmaceutical use.

14. A pharmaceutical composition comprising a purified homodimer according to claim 13 and a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2620 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..1935

( x i ) SEQUENCE DESCRIPTION: SEQ ID NO:1:

-continued

| | | | | | | | | | | | | | | | | |
|---|---|---|---|---|---|---|---|---|---|---|---|---|---|---|---|---|
| GGG | GCC | AGC | TGC | AGC | CTC | AGC | CCC | ACA | AGT | CTT | GCA | GAA | ACA | GTC | CAT | 48 |
| Gly | Ala | Ser | Cys | Ser | Leu | Ser | Pro | Thr | Ser | Leu | Ala | Glu | Thr | Val | His | |
| 1 | | | | 5 | | | | | 10 | | | | | 15 | | |
| TGT | GAC | CTT | CAG | CCT | GTG | GGC | CCC | GAG | AGG | GGC | GAG | GTG | ACA | TAT | ACC | 96 |
| Cys | Asp | Leu | Gln | Pro | Val | Gly | Pro | Glu | Arg | Gly | Glu | Val | Thr | Tyr | Thr | |
| | | | 20 | | | | | 25 | | | | | 30 | | | |
| ACT | AGC | CAG | GTC | TCG | AAG | GGC | TGC | GTG | GCT | CAG | GCC | CCC | AAT | GCC | ATC | 144 |
| Thr | Ser | Gln | Val | Ser | Lys | Gly | Cys | Val | Ala | Gln | Ala | Pro | Asn | Ala | Ile | |
| | | 35 | | | | | 40 | | | | | 45 | | | | |
| CTT | GAA | GTC | CAT | GTC | CTC | TTC | CTG | GAG | TTC | CCA | ACG | GGC | CCG | TCA | CAG | 192 |
| Leu | Glu | Val | His | Val | Leu | Phe | Leu | Glu | Phe | Pro | Thr | Gly | Pro | Ser | Gln | |
| | 50 | | | | | 55 | | | | | 60 | | | | | |
| CTG | GAG | CTG | ACT | CTC | CAG | GCA | TCC | AAG | CAA | AAT | GGC | ACC | TGG | CCC | CGA | 240 |
| Leu | Glu | Leu | Thr | Leu | Gln | Ala | Ser | Lys | Gln | Asn | Gly | Thr | Trp | Pro | Arg | |
| 65 | | | | | 70 | | | | | 75 | | | | | 80 | |
| GAG | GTG | CTT | CTG | GTC | CTC | AGT | GTA | AAC | AGC | AGT | GTC | TTC | CTG | CAT | CTC | 288 |
| Glu | Val | Leu | Leu | Val | Leu | Ser | Val | Asn | Ser | Ser | Val | Phe | Leu | His | Leu | |
| | | | | 85 | | | | | 90 | | | | | 95 | | |
| CAG | GCC | CTG | GGA | ATC | CCA | CTG | CAC | TTG | GCC | TAC | AAT | TCC | AGC | CTG | GTC | 336 |
| Gln | Ala | Leu | Gly | Ile | Pro | Leu | His | Leu | Ala | Tyr | Asn | Ser | Ser | Leu | Val | |
| | | | 100 | | | | | 105 | | | | | 110 | | | |
| ACC | TTC | CAA | GAG | CCC | CCG | GGG | GTC | AAC | ACC | ACA | GAG | CTG | CCA | TCC | TTC | 384 |
| Thr | Phe | Gln | Glu | Pro | Pro | Gly | Val | Asn | Thr | Thr | Glu | Leu | Pro | Ser | Phe | |
| | | 115 | | | | | 120 | | | | | 125 | | | | |
| CCC | AAG | ACC | CAG | ATC | CTT | GAG | TGG | GCA | GCT | GAG | AGG | GGC | CCC | ATC | ACC | 432 |
| Pro | Lys | Thr | Gln | Ile | Leu | Glu | Trp | Ala | Ala | Glu | Arg | Gly | Pro | Ile | Thr | |
| | 130 | | | | | 135 | | | | | 140 | | | | | |
| TCT | GCT | GCT | GAG | CTG | AAT | GAC | CCC | CAG | AGC | ATC | CTC | CTC | CGA | CTG | GGC | 480 |
| Ser | Ala | Ala | Glu | Leu | Asn | Asp | Pro | Gln | Ser | Ile | Leu | Leu | Arg | Leu | Gly | |
| 145 | | | | | 150 | | | | | 155 | | | | | 160 | |
| CAA | GCC | CAG | GGG | TCA | CTG | TCC | TTC | TGC | ATG | CTG | GAA | GCC | AGC | CAG | GAC | 528 |
| Gln | Ala | Gln | Gly | Ser | Leu | Ser | Phe | Cys | Met | Leu | Glu | Ala | Ser | Gln | Asp | |
| | | | | 165 | | | | | 170 | | | | | 175 | | |
| ATG | GGC | CGC | ACG | CTC | GAG | TGG | CGG | CCG | CGT | ACT | CCA | GCC | TTG | GTC | CGG | 576 |
| Met | Gly | Arg | Thr | Leu | Glu | Trp | Arg | Pro | Arg | Thr | Pro | Ala | Leu | Val | Arg | |
| | | | 180 | | | | | 185 | | | | | 190 | | | |
| GGC | TGC | CAC | TTG | GAA | GGC | GTG | GCC | GGC | CAC | AAG | GAG | GCG | CAC | ATC | CTG | 624 |
| Gly | Cys | His | Leu | Glu | Gly | Val | Ala | Gly | His | Lys | Glu | Ala | His | Ile | Leu | |
| | | 195 | | | | | 200 | | | | | 205 | | | | |
| AGG | GTC | CTG | CCG | GGC | CAC | TCG | GCC | GGG | CCC | CGG | ACG | GTG | ACG | GTG | AAG | 672 |
| Arg | Val | Leu | Pro | Gly | His | Ser | Ala | Gly | Pro | Arg | Thr | Val | Thr | Val | Lys | |
| | 210 | | | | | 215 | | | | | 220 | | | | | |
| GTG | GAA | CTG | AGC | TGC | GCA | CCC | GGG | GAT | CTC | GAT | GCC | GTC | CTC | ATC | CTG | 720 |
| Val | Glu | Leu | Ser | Cys | Ala | Pro | Gly | Asp | Leu | Asp | Ala | Val | Leu | Ile | Leu | |
| 225 | | | | | 230 | | | | | 235 | | | | | 240 | |
| CAG | GGT | CCC | CCC | TAC | GTG | TCC | TGG | CTC | ATC | GAC | GCC | AAC | CAC | AAC | ATG | 768 |
| Gln | Gly | Pro | Pro | Tyr | Val | Ser | Trp | Leu | Ile | Asp | Ala | Asn | His | Asn | Met | |
| | | | | 245 | | | | | 250 | | | | | 255 | | |
| CAG | ATC | TGG | ACC | ACT | GGA | GAA | TAC | TCC | TTC | AAG | ATC | TTT | CCA | GAG | AAA | 816 |
| Gln | Ile | Trp | Thr | Thr | Gly | Glu | Tyr | Ser | Phe | Lys | Ile | Phe | Pro | Glu | Lys | |
| | | | 260 | | | | | 265 | | | | | 270 | | | |
| AAC | ATT | CGT | GGC | TTC | AAG | CTC | CCA | GAC | ACA | CCT | CAA | GGC | CTC | CTG | GGG | 864 |
| Asn | Ile | Arg | Gly | Phe | Lys | Leu | Pro | Asp | Thr | Pro | Gln | Gly | Leu | Leu | Gly | |
| | | 275 | | | | | 280 | | | | | 285 | | | | |
| GAG | GCC | CGG | ATG | CTC | AAT | GCC | AGC | ATT | GTG | GCA | TCC | TTC | GTG | GAG | CTA | 912 |
| Glu | Ala | Arg | Met | Leu | Asn | Ala | Ser | Ile | Val | Ala | Ser | Phe | Val | Glu | Leu | |
| | 290 | | | | | 295 | | | | | 300 | | | | | |
| CCG | CTG | GCC | AGC | ATT | GTC | TCA | CTT | CAT | GCC | TCC | AGC | TGC | GGT | GGT | AGG | 960 |
| Pro | Leu | Ala | Ser | Ile | Val | Ser | Leu | His | Ala | Ser | Ser | Cys | Gly | Gly | Arg | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| CTG | CAG | ACC | TCA | CCC | GCA | CCG | ATC | CAG | ACC | ACT | CCT | CCC | AAG | GAC | ACT | 1008 |
| Leu | Gln | Thr | Ser | Pro | Ala | Pro | Ile | Gln | Thr | Thr | Pro | Pro | Lys | Asp | Thr | |
| | | | | 325 | | | | 330 | | | | | 335 | | | |
| TGT | AGC | CCG | GAG | CTG | CTC | ATG | TCC | TTG | ATC | CAG | ACA | AAG | TGT | GCC | GAC | 1056 |
| Cys | Ser | Pro | Glu | Leu | Leu | Met | Ser | Leu | Ile | Gln | Thr | Lys | Cys | Ala | Asp | |
| | | | 340 | | | | | 345 | | | | | 350 | | | |
| GAC | GCC | ATG | ACC | CTG | GTA | CTA | AAG | AAA | GAG | CTT | GTT | GCG | CAT | TTG | AAG | 1104 |
| Asp | Ala | Met | Thr | Leu | Val | Leu | Lys | Lys | Glu | Leu | Val | Ala | His | Leu | Lys | |
| | | | 355 | | | | | 360 | | | | | 365 | | | |
| TGC | ACC | ATC | ACG | GGC | CTG | ACC | TTC | TGG | GAC | CCC | AGC | TGT | GAG | GCA | GAG | 1152 |
| Cys | Thr | Ile | Thr | Gly | Leu | Thr | Phe | Trp | Asp | Pro | Ser | Cys | Glu | Ala | Glu | |
| | 370 | | | | | 375 | | | | | 380 | | | | | |
| GAC | AGG | GGT | GAC | AAG | TTT | GTC | TTG | CGC | AGT | GCT | TAC | TCC | AGC | TGT | GGC | 1200 |
| Asp | Arg | Gly | Asp | Lys | Phe | Val | Leu | Arg | Ser | Ala | Tyr | Ser | Ser | Cys | Gly | |
| 385 | | | | | 390 | | | | | 395 | | | | | 400 | |
| ATG | CAG | GTG | TCA | GCA | AGT | ATG | ATC | AGC | AAT | GAG | GCG | GTG | GTC | AAT | ATC | 1248 |
| Met | Gln | Val | Ser | Ala | Ser | Met | Ile | Ser | Asn | Glu | Ala | Val | Val | Asn | Ile | |
| | | | | 405 | | | | | 410 | | | | | 415 | | |
| CTG | TCG | AGC | TCA | TCA | CCA | CAG | CGG | AAA | AAG | GTG | CAC | TGC | CTC | AAC | ATG | 1296 |
| Leu | Ser | Ser | Ser | Ser | Pro | Gln | Arg | Lys | Lys | Val | His | Cys | Leu | Asn | Met | |
| | | | 420 | | | | | 425 | | | | | 430 | | | |
| GAC | AGC | CTC | TCT | TTC | CAG | CTG | GGC | CTC | TAC | CTC | AGC | CCA | CAC | TTC | CTC | 1344 |
| Asp | Ser | Leu | Ser | Phe | Gln | Leu | Gly | Leu | Tyr | Leu | Ser | Pro | His | Phe | Leu | |
| | | | 435 | | | | | 440 | | | | | 445 | | | |
| CAG | GCC | TCC | AAC | ACC | ATC | GAG | CCG | GGG | CAG | CAG | AGC | TTT | GTG | CAG | GTC | 1392 |
| Gln | Ala | Ser | Asn | Thr | Ile | Glu | Pro | Gly | Gln | Gln | Ser | Phe | Val | Gln | Val | |
| | | 450 | | | | | 455 | | | | | 460 | | | | |
| AGA | GTG | TCC | CCA | TCC | GTC | TCC | GAG | TTC | CTC | CTC | CAG | TTA | GAC | AGC | TGC | 1440 |
| Arg | Val | Ser | Pro | Ser | Val | Ser | Glu | Phe | Leu | Leu | Gln | Leu | Asp | Ser | Cys | |
| 465 | | | | | 470 | | | | | 475 | | | | | 480 | |
| CAC | CTG | GAC | TTG | GGG | CCT | GAG | GGA | GGC | ACC | GTG | GAA | CTC | ATC | CAG | GGC | 1488 |
| His | Leu | Asp | Leu | Gly | Pro | Glu | Gly | Gly | Thr | Val | Glu | Leu | Ile | Gln | Gly | |
| | | | | 485 | | | | | 490 | | | | | 495 | | |
| CGG | GCG | GCC | AAG | GGC | AAC | TGT | GTG | AGC | CTG | CTG | TCC | CCA | AGC | CCC | GAG | 1536 |
| Arg | Ala | Ala | Lys | Gly | Asn | Cys | Val | Ser | Leu | Leu | Ser | Pro | Ser | Pro | Glu | |
| | | | 500 | | | | | 505 | | | | | 510 | | | |
| GGT | GAC | CCG | CGC | TTC | AGC | TTC | CTC | CTC | CAC | TTC | TAC | ACA | GTA | CCC | ATA | 1584 |
| Gly | Asp | Pro | Arg | Phe | Ser | Phe | Leu | Leu | His | Phe | Tyr | Thr | Val | Pro | Ile | |
| | | 515 | | | | | 520 | | | | | 525 | | | | |
| CCC | AAA | ACC | GGC | ACC | CTC | AGC | TGC | ACG | GTA | GCC | CTG | CGT | CCC | AAG | ACC | 1632 |
| Pro | Lys | Thr | Gly | Thr | Leu | Ser | Cys | Thr | Val | Ala | Leu | Arg | Pro | Lys | Thr | |
| | 530 | | | | | 535 | | | | | 540 | | | | | |
| GGG | TCT | CAA | GAC | CAG | GAA | GTC | CAT | AGG | ACT | GTC | TTC | ATG | CGC | TTG | AAC | 1680 |
| Gly | Ser | Gln | Asp | Gln | Glu | Val | His | Arg | Thr | Val | Phe | Met | Arg | Leu | Asn | |
| 545 | | | | | 550 | | | | | 555 | | | | | 560 | |
| ATC | ATC | AGC | CCT | GAC | CTG | TCT | GGT | TGC | ACA | AGC | AAA | GGC | CTC | GTC | CTG | 1728 |
| Ile | Ile | Ser | Pro | Asp | Leu | Ser | Gly | Cys | Thr | Ser | Lys | Gly | Leu | Val | Leu | |
| | | | | 565 | | | | | 570 | | | | | 575 | | |
| CCC | GCC | GTG | CTG | GGC | ATC | ACC | TTT | GGT | GCC | TTC | CTC | ATC | GGG | GCC | CTG | 1776 |
| Pro | Ala | Val | Leu | Gly | Ile | Thr | Phe | Gly | Ala | Phe | Leu | Ile | Gly | Ala | Leu | |
| | | | 580 | | | | | 585 | | | | | 590 | | | |
| CTC | ACT | GCT | GCA | CTC | TGG | TAC | ATC | TAC | TCG | CAC | ACG | CGT | TCC | CCC | AGC | 1824 |
| Leu | Thr | Ala | Ala | Leu | Trp | Tyr | Ile | Tyr | Ser | His | Thr | Arg | Ser | Pro | Ser | |
| | | | 595 | | | | | 600 | | | | | 605 | | | |
| AAG | CGG | GAG | CCC | GTG | GTG | GCG | GTG | GCT | GCC | CCG | GCC | TCC | TCG | GAG | AGC | 1872 |
| Lys | Arg | Glu | Pro | Val | Val | Ala | Val | Ala | Ala | Pro | Ala | Ser | Ser | Glu | Ser | |
| | | 610 | | | | | 615 | | | | | 620 | | | | |
| AGC | AGC | ACC | AAC | CAC | AGC | ATC | GGG | AGC | ACC | CAG | AGC | ACC | CCC | TGC | TCC | 1920 |
| Ser | Ser | Thr | Asn | His | Ser | Ile | Gly | Ser | Thr | Gln | Ser | Thr | Pro | Cys | Ser | |
| 625 | | | | | 630 | | | | | 635 | | | | | 640 | |

```
ACC AGC AGC ATG GCA TAGCCCCGGC CCCCCGCGCT CGCCCAGCAG GAGAGACTGA         1975
Thr Ser Ser Met Ala
            645

GCAGCCGCCA GCTGGGAGCA CTGGTGTGAA CTCACCCTGG GAGCCAGTCC TCCACTCGAC         2035

CCAGAATGGA GCCTGCTCTC CGCGCCTACC CTTCCCGCCT CCCTCTCAGA GGCCTGCTGC         2095

CAGTGCAGCC ACTGGCTTGG AACACCTTGG GGTCCCTCCA CCCCACAGAA CCTTCAACCC         2155

AGTGGGTCTG GGATATGGCT GCCCAGGAGA CAGACCACTT GCCACGCTGT TGTAAAAACC         2215

CAAGTCCCTG TCATTTGAAC CTGGATCCAG CACTGGTGAA CTGAGCTGGG CAGGAAGGGA         2275

GAACTTGAAA CAGATTCAGG CCAGCCCAGC CAGGCCAACA GCACCTCCCC GCTGGGAAGA         2335

GAAGAGGGCC CAGCCCAGAG CCACCTGGAT CTATCCCTGC GGCCTCCACA CCTGAACTTG         2395

CCTAACTAAC TGGCAGGGGA GACAGGAGCC TAGCGGAGCC CAGCCTGGGA GCCCAGAGGG         2455

TGGCAAGAAC AGTGGGCGTT GGGAGCCTAG CTCCTGCCAC ATGGAGCCCC CTCTGCCGGT         2515

CGGGCAGCCA GCAGAGGGGG AGTAGCCAAG CTGCTTGTCC TGGGCCTGCC CCTGTGTATT         2575

CACCACCAAT AAATCAGACC ATGAAACCAG TGAAAAAAAA AAAAA                         2620
```

( 2 ) INFORMATION FOR SEQ ID NO:2:

( i ) SEQUENCE CHARACTERISTICS:
    ( A ) LENGTH: 645 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Gly Ala Ser Cys Ser Leu Ser Pro Thr Ser Leu Ala Glu Thr Val His
 1               5                  10                  15

Cys Asp Leu Gln Pro Val Gly Pro Glu Arg Gly Glu Val Thr Tyr Thr
                20                  25                  30

Thr Ser Gln Val Ser Lys Gly Cys Val Ala Gln Ala Pro Asn Ala Ile
            35                  40                  45

Leu Glu Val His Val Leu Phe Leu Glu Phe Pro Thr Gly Pro Ser Gln
        50                  55                  60

Leu Glu Leu Thr Leu Gln Ala Ser Lys Gln Asn Gly Thr Trp Pro Arg
65                  70                  75                  80

Glu Val Leu Leu Val Leu Ser Val Asn Ser Ser Val Phe Leu His Leu
                85                  90                  95

Gln Ala Leu Gly Ile Pro Leu His Leu Ala Tyr Asn Ser Ser Leu Val
                100                 105                 110

Thr Phe Gln Glu Pro Pro Gly Val Asn Thr Thr Glu Leu Pro Ser Phe
            115                 120                 125

Pro Lys Thr Gln Ile Leu Glu Trp Ala Ala Glu Arg Gly Pro Ile Thr
130                 135                 140

Ser Ala Ala Glu Leu Asn Asp Pro Gln Ser Ile Leu Leu Arg Leu Gly
145                 150                 155                 160

Gln Ala Gln Gly Ser Leu Ser Phe Cys Met Leu Glu Ala Ser Gln Asp
                165                 170                 175

Met Gly Arg Thr Leu Glu Trp Arg Pro Arg Thr Pro Ala Leu Val Arg
            180                 185                 190

Gly Cys His Leu Glu Gly Val Ala Gly His Lys Glu Ala His Ile Leu
        195                 200                 205

Arg Val Leu Pro Gly His Ser Ala Gly Pro Arg Thr Val Thr Val Lys
    210                 215                 220
```

```
Val  Glu  Leu  Ser  Cys  Ala  Pro  Gly  Asp  Leu  Asp  Ala  Val  Leu  Ile  Leu
225                      230                 235                           240

Gln  Gly  Pro  Pro  Tyr  Val  Ser  Trp  Leu  Ile  Asp  Ala  Asn  His  Asn  Met
                    245                 250                      255

Gln  Ile  Trp  Thr  Thr  Gly  Glu  Tyr  Ser  Phe  Lys  Ile  Phe  Pro  Glu  Lys
               260                 265                           270

Asn  Ile  Arg  Gly  Phe  Lys  Leu  Pro  Asp  Thr  Pro  Gln  Gly  Leu  Leu  Gly
          275                      280                      285

Glu  Ala  Arg  Met  Leu  Asn  Ala  Ser  Ile  Val  Ala  Ser  Phe  Val  Glu  Leu
     290                      295                 300

Pro  Leu  Ala  Ser  Ile  Val  Ser  Leu  His  Ala  Ser  Ser  Cys  Gly  Gly  Arg
305                      310                 315                           320

Leu  Gln  Thr  Ser  Pro  Ala  Pro  Ile  Gln  Thr  Thr  Pro  Pro  Lys  Asp  Thr
                    325                 330                           335

Cys  Ser  Pro  Glu  Leu  Leu  Met  Ser  Leu  Ile  Gln  Thr  Lys  Cys  Ala  Asp
               340                 345                           350

Asp  Ala  Met  Thr  Leu  Val  Leu  Lys  Lys  Glu  Leu  Val  Ala  His  Leu  Lys
          355                      360                 365

Cys  Thr  Ile  Thr  Gly  Leu  Thr  Phe  Trp  Asp  Pro  Ser  Cys  Glu  Ala  Glu
     370                      375                 380

Asp  Arg  Gly  Asp  Lys  Phe  Val  Leu  Arg  Ser  Ala  Tyr  Ser  Ser  Cys  Gly
385                      390                 395                           400

Met  Gln  Val  Ser  Ala  Ser  Met  Ile  Ser  Asn  Glu  Ala  Val  Val  Asn  Ile
               405                 410                           415

Leu  Ser  Ser  Ser  Ser  Pro  Gln  Arg  Lys  Lys  Val  His  Cys  Leu  Asn  Met
               420                      425                 430

Asp  Ser  Leu  Ser  Phe  Gln  Leu  Gly  Leu  Tyr  Leu  Ser  Pro  His  Phe  Leu
          435                      440                      445

Gln  Ala  Ser  Asn  Thr  Ile  Glu  Pro  Gly  Gln  Gln  Ser  Phe  Val  Gln  Val
     450                      455                 460

Arg  Val  Ser  Pro  Ser  Val  Ser  Glu  Phe  Leu  Leu  Gln  Leu  Asp  Ser  Cys
465                      470                 475                           480

His  Leu  Asp  Leu  Gly  Pro  Glu  Gly  Gly  Thr  Val  Glu  Leu  Ile  Gln  Gly
               485                      490                      495

Arg  Ala  Ala  Lys  Gly  Asn  Cys  Val  Ser  Leu  Leu  Ser  Pro  Ser  Pro  Glu
               500                 505                      510

Gly  Asp  Pro  Arg  Phe  Ser  Phe  Leu  Leu  His  Phe  Tyr  Thr  Val  Pro  Ile
          515                      520                 525

Pro  Lys  Thr  Gly  Thr  Leu  Ser  Cys  Thr  Val  Ala  Leu  Arg  Pro  Lys  Thr
     530                      535                 540

Gly  Ser  Gln  Asp  Gln  Glu  Val  His  Arg  Thr  Val  Phe  Met  Arg  Leu  Asn
545                      550                 555                           560

Ile  Ile  Ser  Pro  Asp  Leu  Ser  Gly  Cys  Thr  Ser  Lys  Gly  Leu  Val  Leu
                    565                 570                           575

Pro  Ala  Val  Leu  Gly  Ile  Thr  Phe  Gly  Ala  Phe  Leu  Ile  Gly  Ala  Leu
               580                 585                      590

Leu  Thr  Ala  Ala  Leu  Trp  Tyr  Ile  Tyr  Ser  His  Thr  Arg  Ser  Pro  Ser
          595                      600                 605

Lys  Arg  Glu  Pro  Val  Val  Ala  Val  Ala  Ala  Pro  Ala  Ser  Ser  Glu  Ser
     610                      615                 620

Ser  Ser  Thr  Asn  His  Ser  Ile  Gly  Ser  Thr  Gln  Ser  Thr  Pro  Cys  Ser
625                      630                 635                           640
```

-continued

```
Thr  Ser  Ser  Met  Ala
               645
```